United States Patent [19]

Nazre et al.

[11] Patent Number: 5,573,548
[45] Date of Patent: Nov. 12, 1996

[54] SUTURE ANCHOR

[75] Inventors: Aniruddha A. Nazre, Warsaw; Steven L. Krebs, Fort Wayne, both of Ind.; S. Kyle Hayes, Laguna Niguel, Calif.

[73] Assignee: Zimmer, Inc., Warsaw, Ind.

[21] Appl. No.: 257,762

[22] Filed: Jun. 9, 1994

[51] Int. Cl.$^6$ .................................................. A61B 17/04
[52] U.S. Cl. ................................ 606/232; 606/73; 606/74
[58] Field of Search ............................. 606/232, 72–76, 606/219

[56] References Cited

U.S. PATENT DOCUMENTS

| | | | |
|---|---|---|---|
| D. 331,463 | 12/1992 | Rosenberg et al. | D24/145 |
| D. 331,626 | 12/1992 | Hayhurst et al. | D24/145 |
| 2,890,734 | 6/1959 | Mullin | 151/33 |
| 4,632,100 | 12/1986 | Somers et al. | 128/92 |
| 4,669,473 | 6/1987 | Richards et al. | 128/334 C |
| 4,738,255 | 4/1988 | Goble et al. | 128/92 YF |
| 4,741,330 | 5/1988 | Hayhurst | 128/92 YF |
| 4,898,156 | 2/1990 | Gatturna et al. | 606/72 |
| 4,899,743 | 2/1990 | Nicholson et al. | 606/139 |
| 4,946,468 | 8/1990 | Li | 606/232 |
| 4,968,315 | 11/1990 | Gatturna | 606/72 |
| 5,037,422 | 8/1991 | Hayhurst et al. | 606/72 |
| 5,041,129 | 8/1991 | Hayhurst et al. | 606/232 |
| 5,046,513 | 9/1991 | Gatturna et al. | 128/898 |
| 5,100,417 | 3/1992 | Cerier et al. | 606/139 |
| 5,102,421 | 4/1992 | Anspach, Jr. | 606/232 |
| 5,127,785 | 7/1992 | Faucher | 411/453 |
| 5,129,902 | 7/1992 | Goble et al. | 606/65 |
| 5,141,520 | 8/1992 | Goble et al. | 606/232 |
| 5,152,790 | 10/1992 | Rosenberg et al. | 623/13 |
| 5,156,616 | 10/1992 | Meadows et al. | 606/232 |
| 5,176,682 | 1/1993 | Chow | 606/72 |
| 5,192,303 | 3/1993 | Gatturna et al. | 606/232 |
| 5,203,787 | 4/1993 | Noblitt et al. | 606/232 |
| 5,207,679 | 5/1993 | Li | 606/72 |
| 5,217,486 | 6/1993 | Rice et al. | 606/232 |
| 5,224,946 | 7/1993 | Hayhurst et al. | 606/72 |
| 5,236,445 | 8/1993 | Hayhurst et al. | 606/232 |
| 5,246,369 | 9/1993 | Poulmaire | 433/173 |
| 5,258,016 | 11/1993 | DiPoto et al. | 606/232 |
| 5,268,001 | 12/1993 | Nicholson et al. | 606/72 |
| 5,269,809 | 12/1993 | Hayhurst et al. | 606/232 |
| 5,282,802 | 2/1994 | Mahony, III | 606/72 |
| 5,370,662 | 12/1994 | Stone et al. | 606/232 |

FOREIGN PATENT DOCUMENTS

| | | | |
|---|---|---|---|
| 0361756A1 | 4/1990 | European Pat. Off. | A61B 17/56 |
| 0376641A1 | 7/1990 | European Pat. Off. | A61F 2/08 |
| 0574707A1 | 12/1993 | European Pat. Off. | A61B 17/04 |
| 0599772A1 | 6/1994 | European Pat. Off. | A61B 17/04 |

OTHER PUBLICATIONS

Zimmer, Inc.—"Resistance to Suture Abrasion of the Statak Device"—Oct. 25, 1993.
Zimmer, Inc.—"Mini Statak Subcortical Insertion"—Dec. 13, 1993.
Linvatec—"Rotator Cuff Repair with A New Twist"—Orthopaedics Today—Jul. 1993.
Arthrotek—"The Harpoon"—JBJS, Mar. 1994.
Zimmer, Inc.—"Indications Statak™ Soft Tissue Attachment Device"—Before May 1994.
Zimmer, Inc.—"Statak Soft Tissue Attachment Device"—Before May 1994.

*Primary Examiner*—Gary Jackson
*Attorney, Agent, or Firm*—Cary R. Reeves

[57] ABSTRACT

A suture anchor comprises a shaft having a proximal and a distal end. A screw thread extends from the shaft and spirals from the proximal to the distal end. A cross-hole is formed through the shaft and the screw thread near the proximal end. The cross-hole receives a suture which provides a double end of suture to facilitate attachment of soft tissue. In a preferred embodiment, the shaft is tapered from a larger diameter proximally to a smaller diameter distally while the major diameter of the screw thread remains constant over most of its length. The suture anchor contains a driven portion which preferably contains a groove to conduct the suture from the cross-hole to the free end of the driven portion. A driver for the suture anchor having an engagement portion for engaging the driven portion likewise contains a groove so that when the engagement portion engages the driven portion the two grooves align to form an enclosed passageway for conducting the suture as the suture traverses the driven portion.

4 Claims, 2 Drawing Sheets

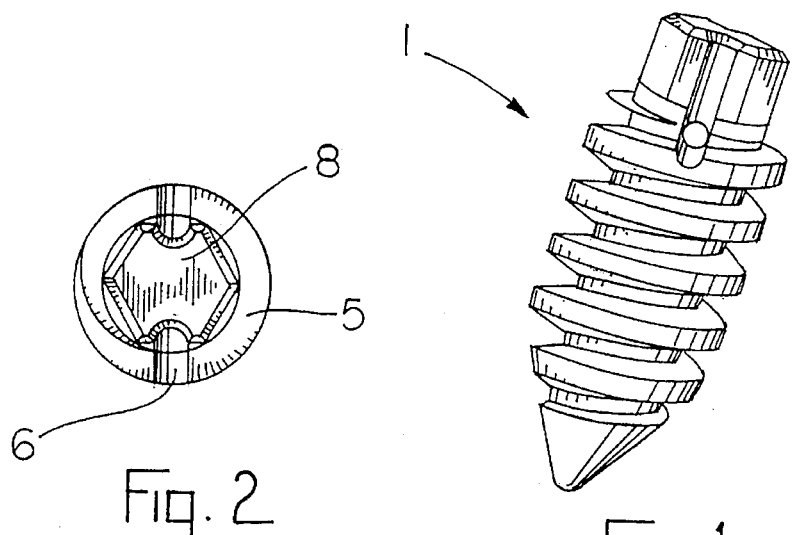
Fig. 1
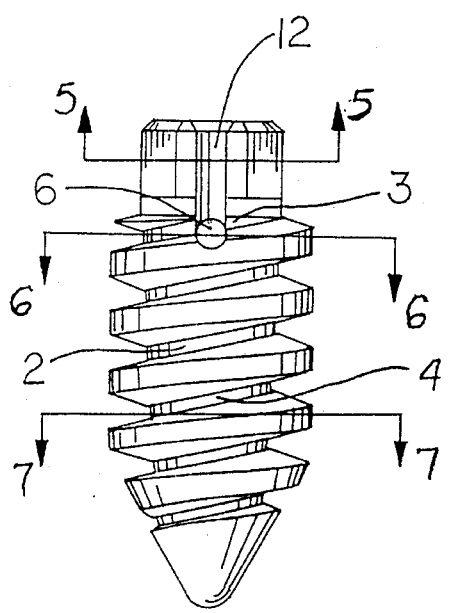
Fig. 2
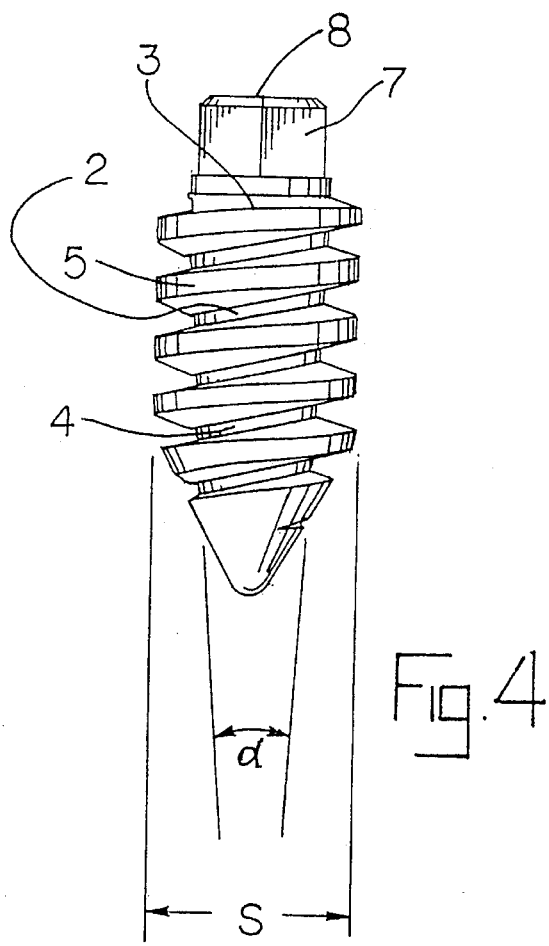
Fig. 3
Fig. 4

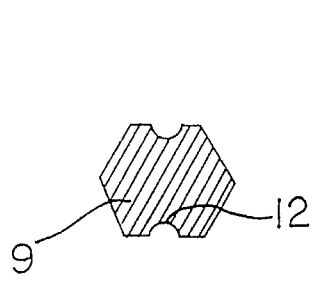
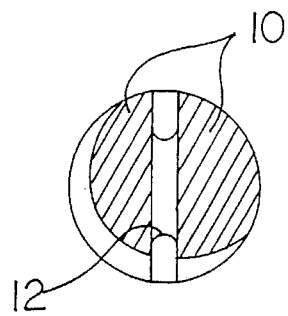
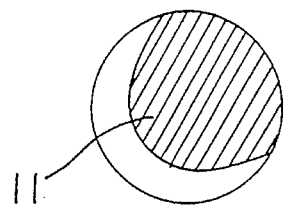
Fig. 5  Fig. 6  Fig. 7
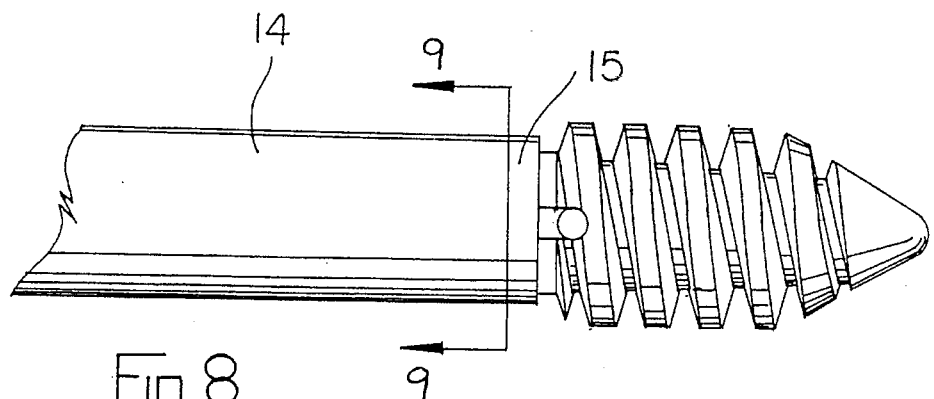
Fig. 8
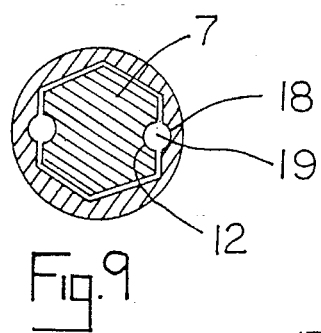
Fig. 9
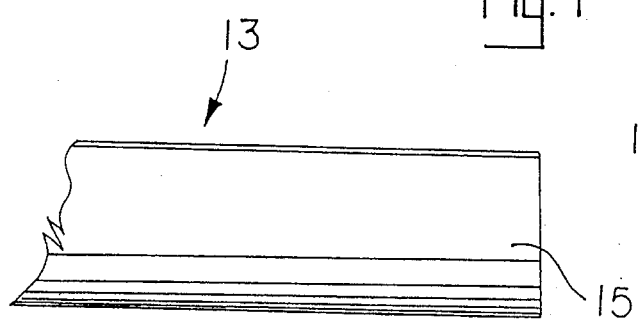
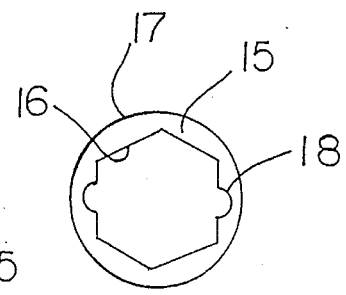
Fig. 10  Fig. 11

SUTURE ANCHOR

BACKGROUND OF THE INVENTION

The present invention relates generally to anchors for securing sutures to bone and more specifically to threaded suture anchors adapted to be screwed into bone.

There are many surgical procedures which require attaching a suture to a bone in order that the suture may be used to hold soft tissue adjacent to the bone. Examples of such procedures include the reattachment and repair of torn tendons and ligaments in the knee, shoulder and hand. Various suture anchors have been proposed and used with varying success. U.S. Pat. No. 4,898,156 teaches a suture anchor with an elastic barb which can be pressed into a hole formed in a bone. A suture is threaded through the suture anchor and is retained in the suture anchor by a knot tied in one end of the suture. The suture anchor resists displacement due to forces on the suture because of the action of the elastic barb in digging into the side of the hole formed in the bone. U.S. Pat. No. 5,102,421 teaches a suture anchor having a series of concentric conical barbs which form a sharp point. The suture anchor is designed to be impacted into the bone. The conical barbs form a hole in the bone as they are driven into the bone and the barbs resist withdrawal of the suture anchor from the hole thus formed. A suture is attached to the suture anchor by crimping an extension of the suture anchor onto one end of the suture. Both of these prior art suture anchors provide a single strand of suture extending from the bone and fixed at one end to the bone.

Others have taught the advantages of a suture anchor secured to bone by the positive and well defined engagement of a helical screw thread with a corresponding thread formed in the bone. U.S. Pat. No. 5,632,100 teaches a suture anchor for turning into a bone. A double end of suture is attached to the suture anchor by securing a knot behind a washer pressed into a hollow end of the suture anchor. A driver engaging surface is also formed within the interior of the hollow end for receiving a driver U.S. Pat. No. 5,156,616 teaches a threaded suture anchor to which a double end of suture is attached. This suture anchor is cannulated longitudinally. The knotted suture is drawn through the cannulation and is retained in the suture anchor because the knot cannot pass through the cannulation. This suture anchor also provides an internal driver engaging surface at one end. Both of these prior art threaded suture anchors retain a suture by trapping a knot within the suture anchor and therefore the suture ends are independently fixed to the anchor. In other words, tension on either of the protruding suture ends is resisted by the knot and tension on one of the ends does not cause the other end to slide through the device.

U.S. Pat. No. Des. 331,463 depicts a threaded suture anchor having an external driver engaging portion and an extending tab for receiving a suture. This configuration for a suture anchor works well for suture anchors which are small or made of delicate materials such as bioresorbable materials. The external driver engaging portion and extending tab for the suture result in a greater cross sectional area in the body of the device than if it were designed like other suture anchors and therefore it is stronger. In addition, since the suture is attached to the anchor by being threaded through an eye in the tab, it is easier for a surgeon to attach his suture of choice to the suture anchor at the time of surgery. Also, where the suture is threaded through an eye, the suture forms a continuous length and tension on one end of the suture tends to cause the other end to slide through the suture anchor. This sliding action is advantageous in some procedures.

However, in very small anchors and especially where delicate materials are used, the extending tab may be overly weak and break under tension. Conversely, the small size of the extending tab may cause it to cut through or kink the suture. Finally, the extending tab requires that the suture anchor be driven more deeply into the bone than a suture anchor without such a tab in order to conceal the tab below the bone surface. This can make it difficult for the suture anchor to purchase cortical bone, especially where the cortical bone is thin.

SUMMARY OF THE INVENTION

The present invention overcomes the disadvantages of prior art devices and provides further advantages by providing a suture anchor with a shaft having a proximal and a distal end. A screw thread extends from the shaft and spirals from the proximal to the distal end. A cross-hole is formed through the shaft and the screw thread near the proximal end. The cross-hole receives a suture which provides a double end of suture to facilitate attachment of soft tissue. The cross-hole allows a surgeon to use his suture of choice and it allows one end of the suture to slide through the cross-hole when the other end is pulled. In addition, the cross-hole is located in an area of relatively large cross section with respect to the suture anchor generally. This results in optimal tensile strength for the suture anchor and provides optimal contact area between the suture anchor and the suture to reduce the likelihood of cutting or kinking the suture. Since there is no extending tab, the anchor need not be driven as deeply as one having a tab. This enhances the attachment of the suture anchor to the bone.

The strength of the suture anchor and the attachment of the suture anchor to the bone are further optimized, in a preferred embodiment, by tapering the shaft from a larger diameter proximally to a smaller diameter distally. This increases the cross sectional area of the suture anchor proximally in the region of the cross-hole to increase strength while increasing the purchase of the threads distally to increase the positive engagement of the threads into the bone distally to increase attachment strength.

The anchor has an externally driven portion adjacent the proximal end. The externally driven portion is stronger than an internally driven portion of the same outside dimensions would be, especially in small sizes or where delicate materials are used. The driven portion preferably contains a groove to conduct the suture from the cross-hole to the free end of the driven portion. A driver for the suture anchor having an engagement portion for engaging the driven portion likewise contains a groove so that when the engagement portion engages the driven portion the two grooves align to form an enclosed passageway for conducting the suture as the suture traverses the driven portion.

BRIEF DESCRIPTION OF THE DRAWINGS

FIG. 1 is a perspective view of the preferred embodiment of the suture anchor of the present invention.

FIG. 2 is a top view of the suture anchor of FIG. 1.

FIG. 3 is a front view of the suture anchor of FIG. 1.

FIG. 4 is a side view of the suture anchor of FIG. 1.

FIG. 5 is a sectional view of the suture anchor of FIG. 3.

FIG. 6 is a sectional view of the suture anchor of FIG. 3.

FIG. 7 is a sectional view of the suture anchor of FIG. 3.

FIG. 8 is a side view of the driver of the present invention in engagement with the suture anchor of the present invention.

FIG. 9 is a sectional view of the suture anchor of FIG. 8.

FIG. 10 is a side view of the driver of the present invention.

FIG. 11 is an end view of the driver of FIG. 10.

DETAILED DESCRIPTION OF THE INVENTION

Referring to FIGS. 1–7, a suture anchor 1 includes a shaft 2 having a longitudinal axis and a proximal end 3 and a distal end 4. Preferably the shaft 2 is solid or, in other words, the shaft 2 is not cannulated along the longitudinal axis. A screw thread 5 extends from the shaft 2 and spirals around the longitudinal axis from the proximal end 3 to the distal end 4. Preferably, the screw thread 5 is continuous and uninterrupted between the proximal end 3 and distal end 4. A driven portion 7 is formed near the proximal end 3 and extends outwardly away from the proximal end 3 and terminates at a free end 8. The driven portion 7 is adapted for positive engagement with a driver so as to facilitate the transmission of torsional loads from the driver to the driven portion 7. The driven portion 7 has a cross-sectional area depicted in FIG. 5. Preferably the driven portion 7 is hexagonal. The shaft and thread have a cross-sectional area depicted in FIG. 6. As can be seen in FIGS. 5 and 6, the cross-sectional area of the shaft 2 and screw thread 5 is larger than the cross-sectional area of the driven portion. A cross-hole 6 extends through the shaft 2 and the screw thread 5, preferably near the proximal end 3. The cross-hole 6 extends through the shaft 2 and screw thread 5 because this region is stronger than the driven portion 7 because of the larger cross-sectional area of the shaft 2 and screw thread 5.

In a preferred embodiment, the shaft 2 forms a tapering minor diameter of the suture anchor 1 and the screw thread 5 has a major diameter S which is constant over most of the length of the suture anchor 1. The shaft 2 preferably tapers linearly from a larger diameter near the proximal end 3 to a smaller diameter near the distal end 4. The included angle α of the tapering shaft 2 is in the range of 4° to 10°, preferably 6° to 7°. In this preferred embodiment, the driven portion 7 has a first cross-sectional area 9. The shaft 2 and screw thread 5 have a second cross-sectional area 10 corresponding approximately to the larger diameter of the tapering shaft 2. The shaft 2 and screw thread 5 have a third cross-sectional area 11 corresponding approximately to the smaller diameter of the tapering shaft 2 and within the length of the constant major diameter S. The second cross-sectional area 10 is greater than both the first cross-sectional area 9 and the third cross-sectional area 11. The cross-hole 6 is formed through the shaft 2 and screw thread 5 near the second cross-sectional area 10. Locating the cross-hole 6 near the largest cross-sectional area of the suture anchor 1 produces the least reduction in tensile strength of the suture anchor 1 and the least likelihood of the suture being cut or kinked by the suture anchor 1. Maintaining a constant major diameter S while tapering the shaft 2 distally, increases the purchase or depth of engagement of the screw thread 5 into the bone toward the distal end 4 of the suture anchor 1. By combining a screw thread 5 having a constant major diameter and a tapering minor diameter with a cross-hole 6 located near the largest cross-sectional area of the suture anchor 1, strength and bone engagement are optimized.

In the preferred embodiment, a groove 12 extends from the proximal end 3 adjacent the cross-hole 6 to the free end 8 of the driven portion 7. The groove 12 allows a suture threaded through the cross-hole 6 to subside into the driven portion 7 and the groove conducts the suture as the suture traverses the driven portion 7.

Referring to FIGS. 8–11, a driver 13 comprises a rod 14 having an engagement portion 15 at an end of the rod 14. The engagement portion 15 has an inner surface 16 and an outer surface 17. The outer surface 17 is preferably smooth and uninterrupted so that it will not abrade or catch tissues adjacent the bone when the driver 13 is turned to drive the anchor 1. The inner surface 16 is adapted for positive engagement with the driven portion 7 so as to facilitate the transmission of torsional loads from the driver 13 to the driven portion 7. The inner surface 16 preferably contains a groove 18. The groove 18 in the inner surface 16 aligns with the groove 12 in the driven portion 7 to form an enclosed passageway 19 for conducting the suture as the suture traverses the driven portion 7 when the engagement portion 15 engages the driven portion 7. The suture material extending beyond the free end 8 of the driven portion 7 is preferably contained inside the driver 13.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A suture anchor for attaching a suture to a bone, the suture anchor being driven by a driver, the suture anchor comprising:

a shaft, the shaft having a longitudinal axis and a proximal end and a distal end;

a screw thread extending from the shaft and spiraling from the proximal end to the distal end, the shaft containing a cross-hole near the proximal end, the cross-hole extending through the shaft and the screw thread; and a driven portion formed adjacent to the proximal end, the driven portion being adapted for positive engagement with the driver so as to facilitate the transmission of torsional loads from the driver to the driven portion wherein the shaft forms a tapering minor diameter of the suture anchor, the shaft tapering linearly from a larger diameter near the proximal end to a smaller diameter near the distal end, the thread having a constant diameter over most of its length, the cross-hole extending through the shaft and the screw thread at the location of the larger diameter.

2. The suture anchor of claim 1, wherein the tapering minor diameter forms an included angle in the range of from 4° to 10°.

3. A suture anchor for attaching a suture to a bone, the suture anchor comprising:

a conical shaft forming a tapering minor diameter of the suture anchor, the shaft having a longitudinal axis and a proximal end and a distal end, the diameter of the shaft near the proximal end being larger than the diameter of the shaft near the distal end;

a driven portion formed adjacent to the proximal end of the shaft and having a first cross-sectional area; and a screw thread extending from the shaft and spiraling the length of the shaft, the screw thread having a major diameter which is constant over most of its length, the shaft and screw thread having a second cross-sectional area corresponding to the area near the proximal end and a third cross-sectional area corresponding to an area having a smaller minor diameter near the distal end but still within the constant major diameter, the shaft tapering smoothly from the second cross-sectional area to the third cross-sectional area, the second cross-sectional area being greater than both the first and third cross-sectional areas, the shaft having a cross-hole extending through the shaft and the screw thread near the second cross-sectional area.

4. In combination:

a suture anchor comprising a shaft, the shaft having a proximal end and a distal end; a screw thread extending from the shaft and spiraling from the proximal end to the distal end, the shaft containing a cross-hole near the proximal end; a driven portion formed adjacent the proximal end; and a driver comprising a rod with an engagement portion at an end of the rod, the engagement portion having an inner surface and an outer surface, the inner surface being adapted for positive engagement with the driven portion so as to facilitate the transmission of torsional loads from the driver to the driven portion, the driven portion and the inner surface forming an enclosed passageway for conducting the suture as the suture traverses the driven portion, when the inner surface engages the driven portion, the driven portion including a groove extending from the proximal end of the shaft adjacent the cross-hole to the free end of the driven portion for conducting the suture as it traverses the driven portion and the inner surface containing a groove, the groove in the inner surface aligning with the groove in the driven portion thus forming the enclosed passageway for conducting the suture as the suture traverses the driven portion when the inner surface engages the driven portion.

\* \* \* \* \*